US00PP18469P3

(12) United States Plant Patent
Houbraken

(10) Patent No.: US PP18,469 P3
(45) Date of Patent: Feb. 5, 2008

(54) ***ARGYRANTHEMUM FRUTESCENS* PLANT NAMED 'ARGYRAYESI'**

(50) Latin Name: *Argyranthemum frutescens*
Varietal Denomination: Argyrayesi

(75) Inventor: Anna M. W. P. Houbraken, Enkhuizen (NL)

(73) Assignee: Syngenta Seeds B.V., Enkhuizen (NL)

( * ) Notice: Subject to any disclaimer, the term of this patent is extended or adjusted under 35 U.S.C. 154(b) by 1 day.

(21) Appl. No.: 11/430,096

(22) Filed: May 8, 2006

(65) Prior Publication Data

US 2007/0261143 P1 Nov. 8, 2007

(51) Int. Cl.
*A01H 5/00* (2006.01)

(52) U.S. Cl. ..... Plt./263

(58) Field of Classification Search ..... Plt./263
See application file for complete search history.

(56) References Cited

U.S. PATENT DOCUMENTS

PP14,577 P2 * 3/2004 Houbraken ..... Plt./263

OTHER PUBLICATIONS

UPOV ROM GTITM Computer Database, GTI Jouve Retrieval Software 2006/04 Citation for Argyrayesi.*

* cited by examiner

*Primary Examiner*—Wendy Haas
(74) *Attorney, Agent, or Firm*—Bruce Vrana

(57) ABSTRACT

A new and distinct cultivar of *Argyranthemum frustescens* plant named 'Argyrayesi' characterized by its upright and rounded plant habit, good field performance, dark green coloured leaves, freely flowering with numerous inflorescences per plant, and daisy-type inflorescences with yellow-colored ray florets and golden yellow-colored disc florets.

1 Drawing Sheet

Latin name of the genus and species of the plant claimed: *Argyranthemum frutescens.*
Varietal denomination: 'Argyrayesi'.

BACKGROUND OF THE NEW PLANT

The present invention relates to a new and distinct cultivar of Marguerite Daisy plant, botanically known as *Argyranthemum frutescens* and hereinafter referred to by the cultivar name 'Argyrayesi.'

The new cultivar is a product of a planned breeding program conducted by the inventor in Enkhuizen, The Netherlands. The new *Argyranthemum* cultivar is compact with an early freely flowering habit, which can be grown without growth regulators.

The new *Argyranthemum* originated from an open-pollination conducted in Enkhuizen, The Netherlands in 2001 of a proprietary selection of *Argyranthemum frutescens* identified as code number 'D0245-1,' not patented, as the female, or seed, parent with an unknown selection of *Argyranthemum frutescens* as the male, or pollen, parent.

The cultivar 'Argyrayesi' was discovered and selected as a single plant within the progeny of the stated open pollination in a controlled environment in Enkhuizen, the Netherlands in August 2002. Asexual reproduction of the new *Argyranthemum* by terminal cuttings in a controlled environment in Enkhuizen, The Netherlands since August 2002, has shown that the unique features of this new *Argyranthemum* are stable and reproduced true to type in successive generations.

SUMMARY OF THE INVENTION

The new *Argyranthemum* has not been observed under all possible environmental conditions. The phenotype may vary somewhat with variations in environment such as temperature and light intensity without, however, any variance in genotype.

The following characteristics have been repeatedly observed and are determined to be basic characteristics of 'Argyrayesi' and distinguish to new *Argyranthemum* as a new and distinct cultivar:

1. Compact, upright and rounded plant habit
2. Freely branching habit and short internodes; dense and bushy plant habit.
3. Early flowering habit
4. Freely flowering habit with numerous inflorescences per plant.
5. Daisy-type inflorescences with yellow-colored ray florets and golden yellow-colored disc florets.

Plants of the new *Argyranthemum* differ primarily from the plants of the female parent selection in the following characteristic:

Plants of the new *Argyranthemum* have a ray floret color of 2B, whereas the plants of the female have a ray floret color of 1D.

TABLE 1

DIFFERENCES BETWEEN THE NEW CULTIVAR 'ARGYRAYESI' AND TWO SIMILAR CULTIVARS

| | 'Argyrayesi' | 'Argyraketis' (U.S. Pat. No. 14,577) | 'Tanja' (Not patented) |
|---|---|---|---|
| Plant Height | 50 cm | 40 cm | 50 cm |
| Plant Width | 70-80 cm | 70-80 cm | 60-70 cm |
| Flower diameter | 3-3.5 cm | 2.2-2.6 cm | 2-3 cm |

TABLE 1-continued

DIFFERENCES BETWEEN THE NEW CULTIVAR 'ARGYRAYESI' AND TWO SIMILAR CULTIVARS

| | 'Argyrayesi' | 'Argyraketis' (U.S. Pat. No. 14,577) | 'Tanja' (Not patented) |
|---|---|---|---|
| Foliage color | 137A | 144A | 144A fading to 12A |
| Peduncle length | 4.5-6 cm | 2-4 cm | 5 cm |

DESCRIPTION OF THE PHOTOGRAPHS

The accompanying color photographs illustrate the overall appearance of the new cultivar, showing the colors as true as it is reasonably possible to obtain in colored reproductions of this type. Colors in the photograph may differ slightly from the color values cited in the detailed botanical description which accurately describe the colors of the new *Argyranthemum.*

DESCRIPTION OF THE NEW CULTIVAR

The aforementioned photographs, following detailed observations and averaged measurements describe plants of this new Marguerite Daisy plant. The data were collected from plants from asexual reproductions carried out in Enkhuizen, The Netherlands. The plant history was taken on 30 weeks old plants, grown in the open field in Enkhuizen, The Netherlands with day temperatures ranging from 16 to 30 degrees C., and night temperatures ranging from 10 to 16 degrees C.

Color references are primarily to The R.H.S. Colour Chart of The Royal Horticultural Society, 1995 Edition, except where general terms of ordinary dictionary significance are used.

The plant:

*Classification.*—Botanical: *Argyranthemum frutescens* cv. 'Argyrayesi'.

Parentage:

*Female parent.*—Proprietary seedling section of *Argyranthemum frutescens,* identified as number 'D0245-1' (not patented). Breeder's code of the new plant is 'E0121-1.'

*Male parent.*—Unidentified section of *Argyranthemum frutescens* (not patented).

Propagation:

*Type cuttings.*—Terminal vegetative cuttings.

*Time to initiated roots.*—7–10 days at air temperature of 21 degrees C.

*Time to develop roots.*—7–14 days at air temperature of 18 degrees C.

*Root description.*—Fibrous, relatively fine, white in color.

*Rooting description.*—Freely branching, dense.

Plant description:

*Growth habit.*—Upright and rounded shape.

*Plant height.*—About 50 cm.

*Vigor.*—Vigorous upright.

*Spreading area of plant.*—About 70–80 cm.

*Strength.*—Very good.

*Branching character.*—Freely branching, plants do not require pinching.

*Crop time.*—About 9 weeks are required to produce a finished flowering plant in a 10.5 cm container from a good developed cutting.

Lateral branch description:

*Length.*—35 cm.

*Diameter.*—8 mm.

*Shape.*—Round, bit grooved.

*Anthocyanin pigmentation.*—Absent.

*Texture.*—Smooth, glabrous.

*Length of internode.*—1.5–4 cm.

*Pubescence.*—Absent.

*Color.*—144A.

The foliage:

*Arrangement.*—Alternate, simple.

*Shape of leaf.*—Bipinnatisect.

*Leaf apex.*—Broadly acute.

*Leaf base.*—Attenuate, clasping.

*Margin.*—Deeply dissected, serrated.

*Texture.*—Thick glabrous smooth.

*Length.*—4.5–5.5 cm.

*Width.*—2–3.5 cm.

*Depth of incision.*—Lanciniate.

*Color.*—Upper side: 137A. Lower side: 143A. Old leaf: 143A.

*Pubescence.*—Absent.

*Petiole.*—Length: About 1–2 cm. Diameter: About 4 mm. Texture: Smooth, glabrous. Color: 137B.

*Venation.*—Shape: Pinnate. Color: 137A.

Inflorescence description:

*Appearance.*—Daisy-type inflorescences with ligulate ray florets. Disc and ray florets develop acropetally on a capitulum. Inflorecences held upright and outwardly on terminal and axillary peduncles. Inflorescences positioned perpendicular to the peduncles. Inflorescences persistent.

*Flowering response.*—Under natural conditions, plant flower from spring to early fall in N-W Europe; plants flower continuous during this period.

*Inflorescence longevity.*—Inflorescences last about ten days on the plant.

*Quantity of inflorescences.*—Freely flowering, about 500 open inflorescences and inflorescence buds per plant.

Flower bud:

*Peduncle.*—Length: 4.5–6 cm. Diameter: 1 mm. Strength: Strong. Aspect: Upright to slightly outward. Texture: Smooth, glabrous. Color: 143C.

*Inflorescence bud.*—Height: 7 mm. Diameter: 8 mm. Shape: Ovoid. Color: 199A.

Inflorescence:

*Size.*—Diameter: 3–3.5 cm. Depth: About 6 mm.

*Diameter of disc.*—About 1.3 cm.

*Form.*—Single flowered.

*Receptacle.*—Height: About 6 mm. Diameter: About 10 mm.

*Involucre/phyllaries.*—3 series of 5 bracts, tightly to receptacle. Appearance: Margins, papery and membranous. Shape: Elliptic. Apex: Broad. Base: Truncate. Texture: Smooth glabrous. Margin: Entire. Length: 3 mm. Width: 2 mm. Color: Upper: 144A, Lower: 139B.

*Fragrance.*—Absent.

Ray florets:

*Shape of ray florets.*—Ligulate.

*Apex.*—Emarginate.

*Base.*—Attenuate.

*Margin.*—Entire.
*Color.*—Upper surface: 2B. Lower surface: 2B.
*No. of ray florets per inflorescene.*—13–16 arranged in a single whorl.
*Size.*—Length: 1.2 cm. Width: 0.4 cm.
*Texture.*—Smooth, glabrous; longitudinally ridged.

Disc florets:
*Arrangement.*—Massed at the center of the inflorescence.
*Shape of disc florets.*—Tubular, elongated, five-pointed; base, fused.
*Color.*—Immature: 14B. Mature: 14B.
*Diameter of disc floret.*—Apex: 1 mm. Base: <1 mm.
*Length of disc floret.*—4 mm.
*Quantity per inflorescence.*—Numerous, ±80.
*Androecium.*—Present only on disc florets.
*Stamen quantity per floret.*—Five.
*Anther length.*—About 1 mm.
*Anther shape.*—Oval.
*Anther color.*—Yellow 21A.
*Pollen color.*—Yellow 21A.
*Amount of pollen.*—Only in disc florets, scarce pollen.
*Gynoecium.*—Present on ray and disc florets.
*Pistil number.*—One per floret.
*Pistil length.*—±3 mm.
*Style color.*—Yellow green 144D.
*Style length.*—±1 mm.
*Stigma color.*—Yellow orange 14A.
*Stigma shape.*—Bilobed.
*Ovary color.*—144C.

Seed/fruit: Seed and fruit production is not observed.

Disease resistance: No susceptibility nor resistance to fungal, bacterial or viral pathogens has been noted. Material is free of virus and *Chrysanthemum* stunt viroid (CSVd).

Temperature/weather tolerance: Plants of the new *Argyanthemum* have been observed to be tolerant to rain, wind and to temperatures from 0° C. to 36° C.

What is claimed is:

1. A new and distinct variety of *Argyranthemum frutescens* plant, named 'Argyrayesi,' substantially as herein illustrated and described.

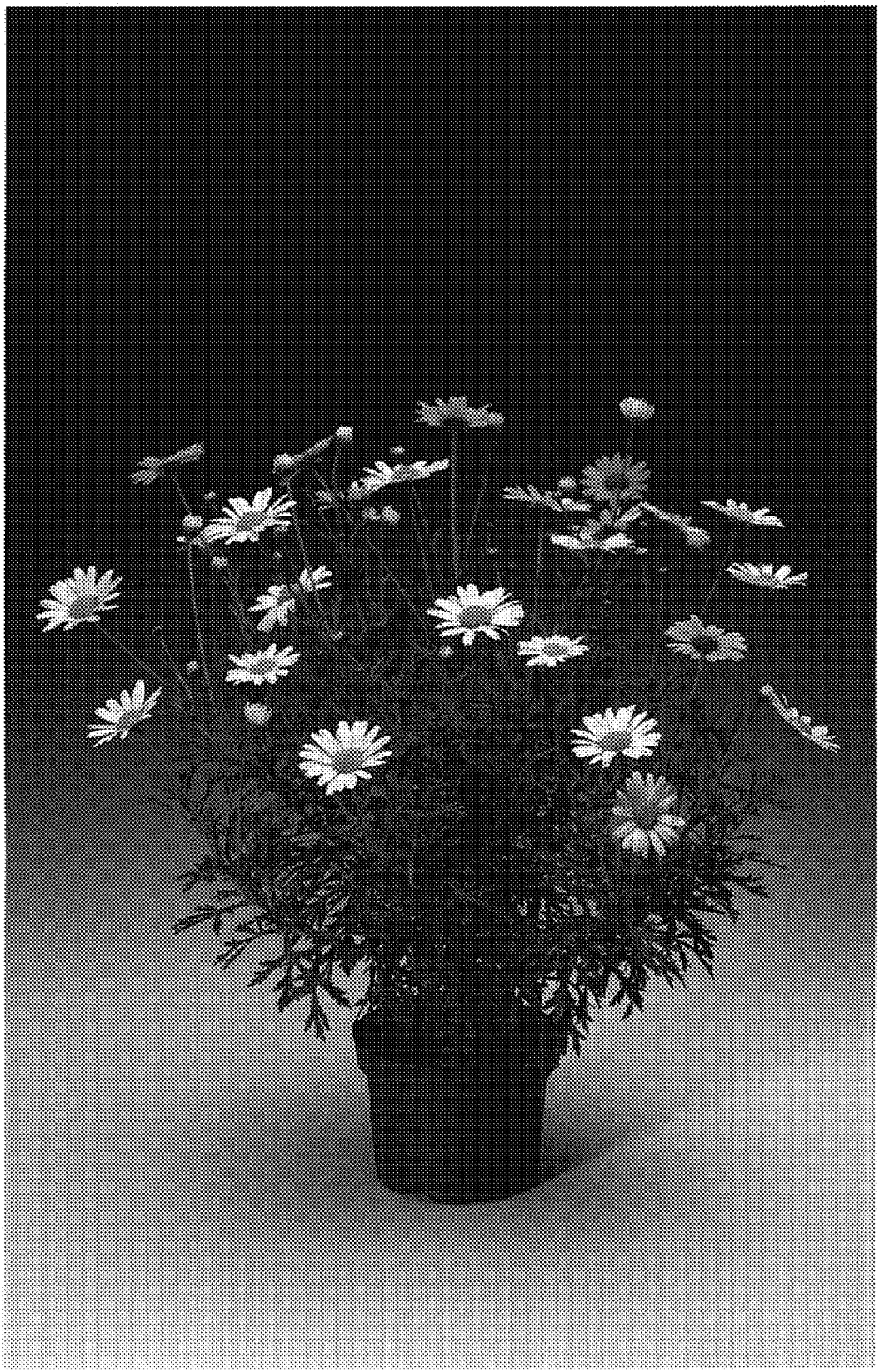

* * * * *